(12) United States Patent
Rebek, Jr. et al.

(10) Patent No.: US 6,939,973 B1
(45) Date of Patent: Sep. 6, 2005

(54) GLYCOLURIL CORE MOLECULES FOR COMBINATORIAL LIBRARIES

(75) Inventors: Julius Rebek, Jr., La Jolla, CA (US); Kent E. Pryor, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 951 days.

(21) Appl. No.: 09/246,468

(22) Filed: Feb. 9, 1999

(51) Int. Cl.[7] .......................................... C07D 403/02
(52) U.S. Cl. .............................. 548/303.4; 548/302.7; 548/303.1
(58) Field of Search .................... 548/302.7, 303.1, 548/303.4

(56) References Cited

U.S. PATENT DOCUMENTS 3,071,591 A * 1/1963 Paterson ................... 260/309.7

FOREIGN PATENT DOCUMENTS

WO    WO 95/19359    11/1995

OTHER PUBLICATIONS

Smeets et al. Synthesis and Binding Proterties of Basket-Shaped Hosts. J. Org. Chem., vol. 54, No. 15, pp. 3710-3717, 1989.*
Rudkevich et al. Chemical Selection and Self-Assembly in a Cyclization Reaction. Angew. Chem. Intl. Ed. Engl., vol. 36, No. 8, pp. 846-848, 1997.*
Ugi, et al., "Multicomponent Reactions in Organic Chemistry", *Endeavor 18*: 115-122 (1994).
Carell, et al., "A Novel Procedure for the Synthesis of Libraries Containing Small Organic Molecules", *Angew. Chem. Int. Ed. Engl. 33*: 2059-2061 (1994).
Carell, et al., "A Solution-Phase Screening Procedure for the Isolation of Active Compounds from a Library of Molecules", *Angew. Chem. Int. Ed. Engl. 33*: 2061-2064 (1994).
Smith, et al., "Synthesis and Biological Evaluation of a Library Containing Potentially 1600 Amides/Esters. A Strategy for Rapid Compound Generation and Screening.", *Bioorg. Med. Chem. Lett. 4*: 2821-2824 (1994).
Pirrung, et al., "Preparation and Screening Against Acetylcholinesterase of a Non-Peptide "Indexed" Combinatorial Library", *J. Am. Chem. Soc. 117*: 1240-1245 (1995).
Carell, et al., "New Promise in Combinatorial Chemistry: Synthesis, Characterization, and Screening of Small-Molecule Libraries in Solution", *Chem. Biol. 2*: 171-183 (1995).
Pirrung, et al., "Discovery of a Novel Tetrahydroacridine Acetylcholinesterase Inhibitor Through an Indexed Combinatorial Library", *Chem. Biol. 2*: 621-626 (1995).
Han, et al., "Liquid-Phase Combinatorial Synthesis", *Proc. Natl. Acad. Sci. USA 92*: 6419-6423 (1995).
Dunayevskiy, et al., "Characterization of the Complexity of Small-Molecule Libraries by Electrospray Ionization Mass Spectrometry", *Anal. Chem. 67*: 2906-2915 (1995).
Früchtel, et al., "Organic Chemistry on Solid Supports", *Angew. Chem. Int. Ed. Engl. 35*: 17-42 (1996).

(Continued)

*Primary Examiner*—Padmashri Ponnaluri
*Assistant Examiner*—Mark L. Shibuya
(74) *Attorney, Agent, or Firm*—Thomas Fitting; Thomas E. Northrup

(57) ABSTRACT

The present invention provides novel glycoluril derivatives for use as core molecules in combinatorial chemistry. Core molecules of the present invention can contain from one to six building blocks. Preferred building blocks are substituted amine radicals. Combinatorial libraries containing such core molecules are also provided.

15 Claims, 11 Drawing Sheets

OTHER PUBLICATIONS

Armstrong, et al., "Multiple-Component Condensation Strategies for Combinatorial Library Synthesis", *Acc. Chem. Res. 29*: 123-131 (1996).

Boger, et al., "Generalized Dipeptidomimetic Template: Solution Phase Parallel Synthesis of Combinatorial Libraries", *J. Am. Chem. Soc. 118*: 2109-2110 (1996).

Cheng, et al., "Novel Solution Phase Strategy for the Synthesis of Chemical Libraries Containing Small Organic Molecules", *J. Am. Chem. Soc. 118*: 2567-2573 (1996).

Keating, et al., "Postcondensation Modifications of Ugi Four-Component Condensation Products: 1-Isocyanocyclohexene as a Convertible Isocyanide. Mechanism of Conversion, Synthesis of Diverse Structures, and Demonstration of Resin Capture", *J. Am. Chem. Soc. 118*: 2574-2583 (1996).

Hermkens, et al., "Solid-Phase Organic Reactions: A Review of the Recent Literature", *Tetrahedron 52*: 4527-4554 (1996).

Wrighton, et al., "Small Peptides as Potent Mimetics of the Protein Hormones Erythropoietin", *Science 273*: 458-463 (1996).

Livnah, et al., "Functional Mimicry of a Protein Hormone by a Peptide Agonist: The EPO Receptor Complex at 2.8 Å", *Science 273*: 464-471 (1996).

Shipps, et al., "Solution-Phase Generation of Tetraurea Libraries", *Bioorg. Med. Chem. 4*: 655-657 (1996).

Cheng, et al., "A Solution-Phase Strategy for the Synthesis of Chemical Libraries Containing Small Organic Molecules: A Universal and Dipeptide Mimetic Template", *Bioorg. Med. Chem. 4*: 727-737 (1996).

Thompson, et al., "Synthesis and Applications of Small Molecule Libraries", *Chem. Rev. 96:* 555-600 (1996).

Pryor, et al., "The Activated Core Approach to Combinatorial Chemistry: A Selection of New Core Molecules", *Tetrahedron 54*: 4107-4124 (1998).

\* cited by examiner

8

17  18

GLYCOLURIL CORE MOLECULES FOR COMBINATORIAL LIBRARIES

Funds used to support some of the work reported herein were provided by the National Institutes of Health under Grant No. GM 27932. The United States government may therefore have certain rights in the disclosed invention.

TECHNICAL FIELD OF THE INVENTION

The field of this invention is combinatorial chemistry. More particularly, the present invention pertains to novel core molecules used as supports for construction of a combinatorial library.

BACKGROUND OF THE INVENTION

The synthesis of new core molecules is often undertaken to provide different orientations of the attached building blocks, thereby increasing structural diversity. The properties of the core molecule have (in several assays) been critical to activity, as libraries made with the same building blocks and linkages have had very different activity levels (Carell et al. *Chem. Biol.* 1995, 2, 171–183). We have previously demonstrated the use of 1, 3, 5, 7-cubanetetracarboxylic acid chloride (Carell et al. *Angew. Chem., Int. Ed. Engl.* 1994, 33, 2059–2061; Eaton et al. *Angew. Chem., Int. Ed. Engl.* 1992, 31, 1421–1436; Bashir-Hashemi, A. *Angew. Chem., Int. Ed. Engl.* 1993, 32, 612–613) and both 9,9-dimethyl-2, 4, 5, 7-xanthenetetracarboxylic acid chloride and tetraisocyanate as cores for combinatorial chemistry (Carell et al. *Chem. Biol.* 1995, 2, 171–183; Carell et al. *Angew. Chem., Int. Ed. Engl.* 1994, 33, 2061–2064; Carell et al. *Angew. Chem., Int. Ed. Engl.* 1994, 33, 2059–2061; Shipps et al. *Bioorg. Med. Chem.* 1996, 4, 655–657; Pryor et al. *Tetrahedron* 1998, 54(16), 4107–4124).

The fact that the certain receptors and proteins appear to bind their ligands utilizing small clusters of residues for the majority of the binding interaction has led to the expectation that small molecules may be capable of triggering a receptor response. It has been anticipated that the generation of detailed knowledge concerning the dimerization modes and ligand binding domains of single transmembrane domain receptors will provide a basis for the design of functional agonists as well as ligand antagonists. However, the non-contiguous and multiple binding domains involved in both the protein-protein and ligand-protein interactions make it difficult to assess the dimerization mode or ligand binding domains in the absence of three-dimensional structural information. This is especially true considering the size of the typical endogenous ligands including proteins such as EPO (166 residues) which themselves contain noncontiguous binding domains which intereact with both subunits of the dimerized receptor.

Recently, the successful identification of cyclic polypeptides with the capacity to mimic the action of EPO was reported, together with details of the intricate receptor-ligand and receptor-receptor interactions in the bound complex (Wrighton et al. *Science* 1996, 273, 458; Livnah et al. *Science* 1996, 273, 464). Although these results represent a major achievement, the size (2 to 20 residues) and nature of ligands identified would not seem to be immediately applicable as drug candidates.

In a recently published PCT application (Rebek et al. WO 95/19359), a process for making xanthene or cubane based compounds and protease inhibitors is described. More particularly, methods for forming combinatorial libraries and the libraries produced are provided. According to a preferred aspect of the invention, a plurality of core molecules, the core molecule being a xanthene or cubane derivative, are reacted with a plurality of different "tool" molecules to form a library of molecules having non-naturally occurring molecular diversity. The libraries are useful for identifying lead compounds which modulate the functional activity of a biological molecule. Protease inhibitors that have been isolated from the libraries also are disclosed.

Combinatorial chemistry, introduced for polypeptide and oligonucleotide libraries, has undergone a rapid development and acceptance. It is widely recognized that this approach, when applied to generating non-peptide small molecule diversity, has provided a new paradigm for drug discovery. Perhaps as a consequence of the extension of the concept from peptide and oligonucleotide synthesis, the majority of applications have relied on solid-phase synthesis and methodological advances continue to extend common synthetic transformations to polymer-supported versions (Thompson et al. *J. A. Chem. Rev.* 1996, 96, 555; Friichtel et al. *Angew. Chem., Int. Ed. Engl.* 1996, 35, 17; Hermkens et al. *Tetrahedron* 1996, 52, 4527).

A less frequently used complement to adapting solution-phase chemistry to polymer-supported combinatorial synthesis is the development of protocols for solution-phase combinatorial synthesis (Han et al. *Proc. Natl. Acad. Sci. U.S.A.* 1995, 92, 6419). Preceding the disclosure of efforts on the the development of a multi-step solution-phase parallel synthesis of chemical libraries (Cheng et al. *J. Am. Chem. Soc.* 1996, 118, 2567; Boger et al. *J. Am. Chem. Soc.* 1996, 118, 2109; Cheng et al. *Bioorg. Med. Chem.* 1996, 4, 727, Tetrahedron Paper and Patent), the single-step solution-phase synthesis of combinatorial libraries was detailed by at least three groups as follows. Smith and coworkers (Smith et al. *Bioorg. Med. Chem. Lett.* 1994, 4, 2821), prepared a library of potentially 1600 amides by reacting 40 acid chlorides with 40 nucleophiles. The library was screened as 80 sample mixtures in a matrix format, allowing immediate deconvolution.

A similar sub-library format was used by Pirrung and Chen (Pirrung et al. *J. Am. Chem. Soc.* 1995, 117, 1240; Pirrung et al. *Chem. Biol.* 1995, 2, 621) who prepared a series of carbamate mixtures which were screened for acetylcholinesterase inhibitory activity. Prior to these efforts, we have disclosed the single-step construction of large libraries presenting amino acid derivatives attached to rigid core templates with a reliance on amide or urea bond formation (Carell et al. *Angew. Chem., Int. Ed. Engl.* 1994, 33, 2059; Carell et al. *Bioorg. Med. Chem.* 1996, 4, 655; Dunayevskiy et al. *Anal. Chem.* 1995, 67, 2906; Carell et al. *Chem. Biol.* 1995, 2, 171). Because of the complexity of the combinatorial libraries resulting from this approach (approaching 100,000 members), an iterative selection strategy based on structural grouping of the building blocks was devised.

In addition to recent advances in this work, substantial progress towards using solution-phase multicomponent reactions for generating combinatorial mixtures has been disclosed. For example, both Ugi and Armstrong have reported four-component condensations including the incorporation of a modifiable isocyanide in combination with resin capture strategy, to provide useful solution-phase library preparations (Ugi et al. *Endeavour* 1994, 18, 115; Keating et al. *J. Am. Chem. Soc.* 1996, 118, 2574; Armstrong et al *Acc. Chem. Res.* 1996, 29, 123).

There remains a need in the art, however, for small molecule libraries of chemical compounds and economical methods for producing such libraries for use in protein and receptor targets as described above. Furthermore, what is needed is an economical method for the identification or deconvolution of these active chemical libraries to rapidly determine active components.

BRIEF SUMMARY OF THE INVENTION

In one aspect, the present invention provides a core molecule for use in constructing a combinatorial library. The core molecule has the structure I, below:

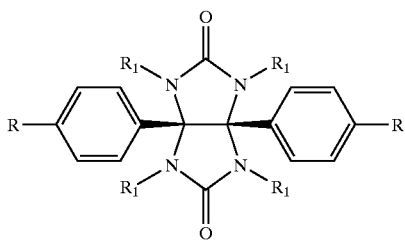

I

In Structure I, each R is independently hydrogen or —O—$R_1$. Each $R_1$ is independently hydrogen or —$CH_2COOR_2$, where $R_2$ is hydrogen or a $C_1$–$C_9$ hydrocarbon. Preferably, the hydrocarbon is a $C_1$–$C_6$ alkyl, a $C_1$–$C_6$ alkenyl, a $C_1$–$C_6$ alkynyl, a $C_6$ aryl, or a $C_6$–$C_9$ aralkyl. This invention further provides a soluble combinatorial library wherein each library member comprises a core molecule of this invention and a building block. In a preferred embodiment, the building block is a substituted amine radical.

BRIEF DESCRIPTION OF THE DRAWINGS

In the drawings that form a portion of the specification.

DETAILED DESCRIPTION OF THE INVENTION

I. The Invention

Figure 1:
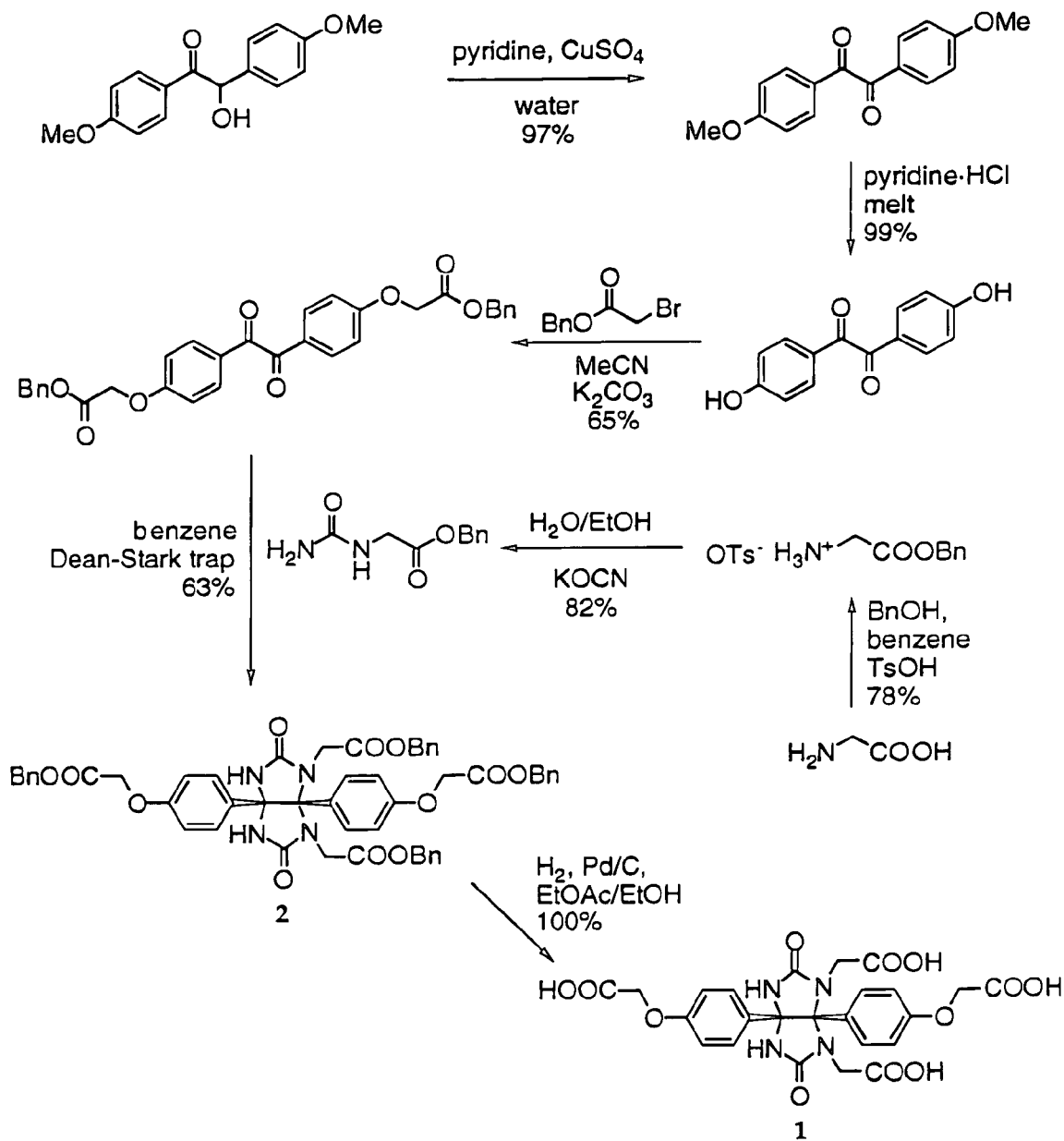
FIG. 1 shows the synthesis of certain tetrasubstituted glycoluril core molecules.

The invention provides novel core molecules suitable for use in combinatorial organic chemistry and the use of those core molecules in preparing and deconvoluting combinatorial libraries. Furthermore, the invention is directed to deconvolution strategies used to simplify complex libraries and build individual molecular species based on these cores. The core molecules represent an attempt to further explore shape-space and increase the structural diversity of prepared libraries, as well as to incorporate recognition elements in the cores to increase the chances for interaction with biological targets.

II Core Molecules

A core molecule of this invention is a derivative of a glycouril and has the structure shown below.

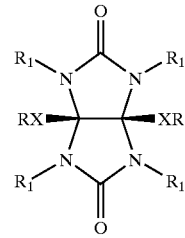

R and $R_1$ represent the putative sites of attachment of library members (e.g., building blocks) to the core molecule. The structure shows six possible sites of attachment. In a preferred embodiment, from 2 to 4 sites are used at any given time for attachment. Where a given site is not used for attachment to a library member, a hydrogen replaces R or $R_1$.

X can be a $C_1$–$C_6$ alkyl, $C_1$–$C_6$ alkenyl, $C_1$–$C_6$ alkynyl, $C_6$ aryl, or $C_6$–$C_9$ aralkyl. X can be linear or cyclic and can be unsubstituted or substituted at each carbon atom with, for example, a halogen. In a preferred embodiment, X is phenyl. In accordance with this embodiment, a core molecule has the structure below

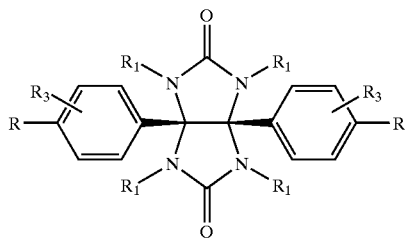

where R, $R_1$ and X have the meaning set forth above. $R_3$ can be hydrogen, a straight or branched $C_1$–$C_6$ linear alkyl (unsubstituted or substituted with a halogen), or a $C_1$–$C_6$ alkoxy. The $R_3$ group can be joined to any of the cyclic carbon atoms that are not linked to R. Each R is thus independently hydrogen or —O—$R_1$. $R_1$ is hydrogen or $CH_2COO$—$R_2$, where each $R_2$ is independently hydrogen, $C_1$–$C_6$ alkyl, $C_1$–$C_6$ alkenyl, $C_1$–$C_6$ alkynyl, $C_6$ aryl, or $C_6$–$C_6$ aralkyl. $R_2$ can be linear or cyclic. $R_2$ can be unsubstituted or substituted at one or more carbon atoms with, for example, a halogen. A preferred halogen is fluoride (F).

An "alkyl" group refers to a saturated aliphatic hydrocarbon, including straight-chain, branched-chain, and cyclic alkyl groups. The alkyl group may have 1 to 12 carbons, or may have 3 to 9 carbons. The alkyl group may be substituted or unsubstituted. When substituted, the substituted groups may be hydroxyl, cyano, halogen, alkoxy, =O, =S, $NO_2$ or $N(CH_3)_2$, amino, SH, SR', or aryl where R' is alkyl ayrl or aralkyl.

An "alkenyl" group refers to an unsaturated hydrocarbon group containing at least one carbon-carbon double bond, including straight-chain, branched-chain, and cyclic groups. The alkenyl group may have 2 to 12 carbons, or may have 3 to 9 carbons. The alkenyl group may be substituted or unsubstituted. When substituted the substituted groups may be hydroxyl, cyano, halogen, alkoxy, =O, =S, $NO_2$ or $N(CH_3)_2$, amino, SH, or SR', or aryl.

An "alkynyl" group refers to an unsaturated hydrocarbon group containing at least one carbon-carbon triple bond, including straight-chain, branched-chain, and cyclic groups. The alkynyl group may have 2 to 12 carbons, or may have 3 to 9 carbons. The alkynyl group may be substituted or unsubstituted. When substituted the substituted groups may be hydroxyl, cyano, halogen, alkoxy, =O, =S, $NO_2$ or $N(CH_3)_2$, amino, SH, SR', or aryl.

An "alkoxy" group refers to an "—O-alkyl" group, where "alkyl" is defined as described above.

An "aryl" group refers to an aromatic group which has at least one ring having a conjugated pi electron system and includes carbocyclic aryl, heterocyclic aryl and biaryl groups, all of which may be optionally substituted. The substituents of the aryl groups may be hydroxyl, cyano, halogen, alkoxy, alkyl, alkenyl, alkynyl, amino, or aryl groups.

An aralkyl group refers to an alkyl (as described above) covalently bonded to an aryl group (as described above).

Carbocyclic aryl groups are groups wherein the ring atoms in the aromatic ring are all carbon atoms. The carbon atoms are optionally substituted. Carbocyclic aryl groups include monocyclic carbocyclic aryl groups and optionally substituted naphthyl groups.

An "amide" refers to an —C(O)—NR"R'", where each of R" and R'" are alkyl, aryl, aralkyl or hydrogen.

An "ester" refers to an —C(O)—OR', where R' may be alkyl, aryl, or aralkyl.

An "amine" refers to a —N(R")R'", where R" and R'", may be independently hydrogen, alkyl, aryl, or aralkyl.

An ether refers to R—O—R, where R is either alkyl, aryl, or aralkyl.

In a preferred embodiment, each $R_3$ is hydrogen and a compound of this invention corresponds to Structure I, below, where R, $R_1$ and $R_2$ are the same as defined above.

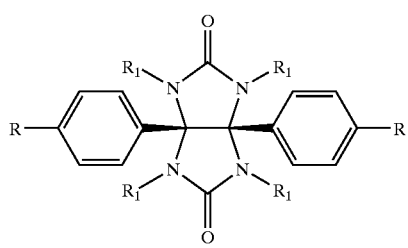

While a compound of Structure I can be linked to 6 building blocks, it is preferred that Structure I contain from 2 to 4 building blocks. Those 2 to 4 building blocks can be linked to Structure I at any of the 6 positions indicated. Thus, preferred compounds corresponding to Structure I are shown below as Structures II, III, IV, V, and VI. Especially preferred core molecules are shown in FIGS. 1, 2, 3, 5, 7 and 9.

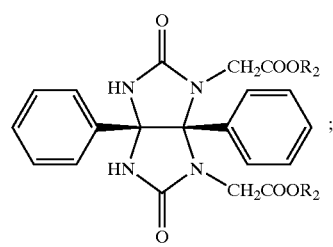

II

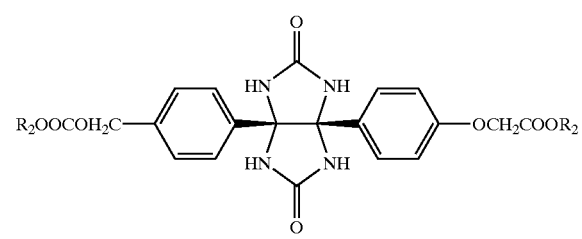

III

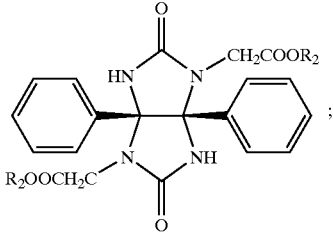

IV

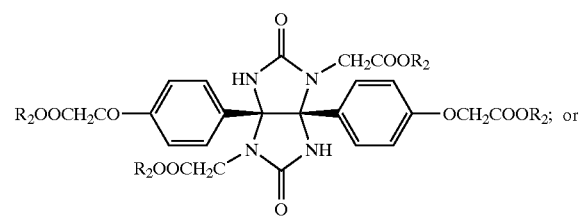

V

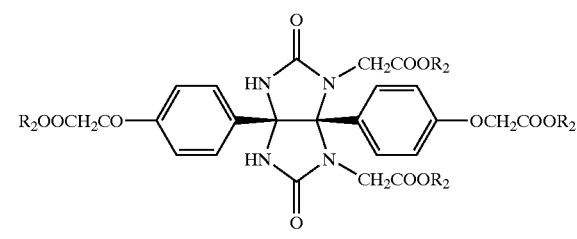

VI

The present invention further provides combinatorial libraries wherein each of the library members comprises a substituted core molecule as set forth below.

Each core molecule can be linked to from 1 to 6 building blocks. The building blocks linked to a given core molecule can be the same or different. Preferably, each core molecule is linked to from 2 to 4 building blocks. A member of such a library thus has the Structure VII, shown below.

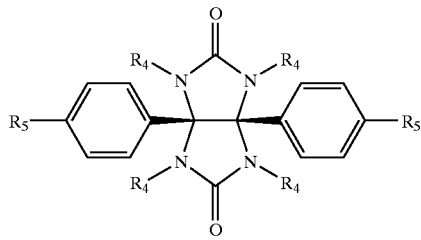

VII

In Structure VII, each R₄ is independently hydrogen or —CH₂COA and each R₅ is independently hydrogen or —OCH₂COA, where A is a building block. Any building block can be used to construct a library so long as that building block is reactive with an activated carboxylic acid group. In a preferred embodiment, the building blocks are substituted amine radicals. Primary and secondary amine radicals are preferred. As used herein, the term "substituted amine radical" means that at least one atom bound to the amine nitrogen is not hydrogen. Such substituted amine radicals are well known in the art. Exemplary such substituted amine radicals are 2-amino-5-diethylaminopentane, 2(2-aminoethyl)-1-methylpyrrolidine, 1-(2-aminoethyl)-Pyrrolidine, 4-(2-aminoethyl)morpholine, 2-(2-aminoethyl)-pyridine, 1-amino-4-methylpiperazine, 4-amino morpholine, furfurylamine, 4-methoxybenylamine, 1-aminopiperidine, 4-(aminoethyl)pyridine, amino acids or derivatives thereof (e.g., H-Ala-OMe, H-AlaOtBu, H-Asn-OtBu, H-Asp(OMe)-OtBu, H-Asp(OtBu)-OtBu, H-Glu (OtBu).OtBu, HGly-OMe, H-Ile-OMe, H-Ile-OtBu, H-Leu-OtBu, H-Lys(BOC)—OMe, H-Lys(BOC)OtBu, H-Met-OMe, H-Phe-OtBu, H-Pro-OtBu, H-Ser(tBu).OtBu-H-Ser-OMe, HThr(tBu)-OMe, H-Tyr-OMe, H-Val-OMe, H-Val-OtBu, H-Tyr(tBu)-OMe, H-Ser(tBu)OMe), Aniline, Benzylamine, Phenethylamine, 2,2-diphenyl ethylamine, Isobutylamine, Butylamine, N,N-diethylethylenediamine, 3-(dimethylamino)propylamine, Aminomethyl cyclopropane, 4-amino-1-benzyl piperidine, 4-(3-aminopropyl)morpholine, 1-(3-aminopropyl)-2-pyrrolidinone, and Ethyl 4-amino-1-piperidine carboxylate.

Especially preferred amine building blocks are 2-amino-5-diethylaminopentane, 2(2-aminoethyl)-1-methylpyrrolidine, 1-(2-aminoethyl)-Pyrrolidine, 4-(2-aminoethyl)morpholine, 2-(2-aminoethyl)-pyridine, 1-amino-4-methylpiperazine, 4-amino morpholine, furfurylamine, 4-methoxybenylamine, 1-aminopiperidine, 4(aminoethyl) pyridine, Aniline, Benzylamine, Phenethylamine, 2,2-diphenyl ethylamine, Isobutylamine, Butylamine, N,N-diethylethylenediamine, 3-(dimethylamino)propylamine, Aminomethyl cyclopropane, 4-amino-1-benzyl piperidine, 4-(3-aminopropyl)morpholine, 1-(3-aminopropyl)-2-pyrrolidinone, and Ethyl 4-amino-1-piperidine carboxylate.

A combinatorial library of this invention is useful for rapidly generating and developing large numbers of drug candidate molecules. The invention is useful for systematically synthesizing a large number of molecules that may vary greatly in their chemical structure or composition, or that may vary in minor aspects of their chemical structure or composition. The invention is also useful for randomly generating a large number of drug candidates, and later optimizing those candidates that show the most medicinal promise. A soluble combinatorial library of the present invention may be screened by any method well known in the art. These methods include, but are not limited to, ELIZA plating, receptor binding, southern, western and northern blotting, and competitive binding.

One such method for identifying an agent to be tested for an ability to bind to and potentially modulate a cellular receptor signal transduction pathway is as follows. The method involves exposing at least one compound from the combinatorial libraries of the present invention to a protein comprising a functional portion of a cellular receptor for a time sufficient to allow binding of the combinatorial library compound to the functional portion of the cellular receptor; removing non-bound compound; and determining the presence of the compound bound to the functional portion of the cellular receptor, thereby identifying a compound to be tested for an ability to modulate a cellular receptor signal transduction pathway.

One method utilizing this approach that may be pursued in the isolation of such receptor-binding molecules would include the attachment of a combinatorial library molecule, or a portion thereof, to a solid matrix, such as agarose or plastic beads, microtiter wells, petri dishes, or membranes composed of, for example, nylon or nitrocellulose, and the subsequent incubation of the attached combinatorial library molecule in the presence of a potential combinatorial library molecule-binding compound or compounds. Attachment to said solid support may be direct or by means of a combinatorial-library-compound-specific antibody bound directly to the solid support. After incubation, unbound compounds are washed away, component-bound compounds are recovered. By utilizing this procedure, large numbers of types of molecules may be simultaneously screened for receptor-binding activity. A number of libraries based on this core have been synthesized. HPLC analysis of small libraries indicates clean reactions with approximately statistical product distributions.

A core molecule of this invention is typically made as an acid (e.g., diacid or tetraacid) where R₂ of Structures II-VI is hydrogen. A number of synthetic routes can be used to prepare such acids. By way of example, acids can be prepared by saponifying the corresponding ethyl or benzyl esters. Alternately, acids can be formed via hydrogenolysis of corresponding benzyl esters. Preparation of a tetraacid core molecule (Compound 1) using hydrogenolysis is shown in FIG. 1. The tetraacid, Compound 1, was originally synthesized by saponification of the corresponding tetraethyl ester. However, Compound 1 proved to be so highly water soluble that separation of the compound from the salt by-products of the reaction was difficult. By replacing the ethyl esters with benzyl esters (compound 2) and performing a hydrogenolysis instead of a saponification Compound 1 was accessible cleanly and in high yields.

Figure 2:
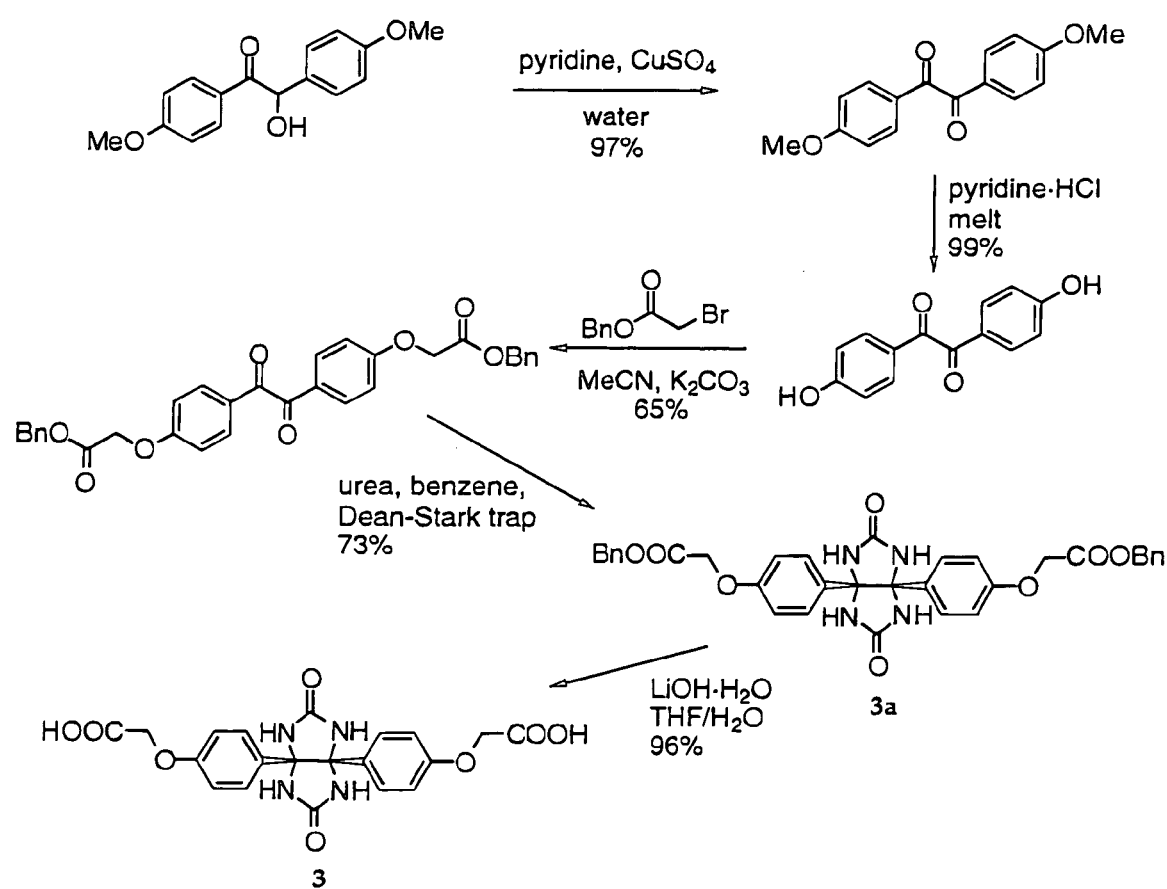
FIG. 2 shows the synthesis of certain disubstituted glycoluril core molecules.
Figure 3:
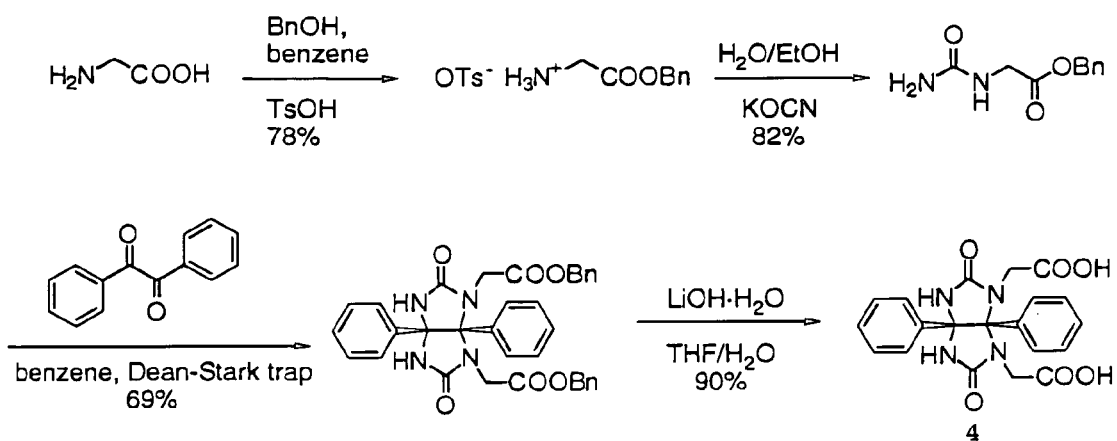
FIG. 3 shows the synthesis of certain disubstituted glycoluril core molecules.

Armed with the knowledge of the glycoluril tetraacid's remarkable water solublity, initial syntheses of other analogs with fewer acid substituents were originally based on the hydrogenolysis of the corresponding benzyl esters, as well (See FIGS. 2 and 3). However, the solubility of the diacid compounds 3 (FIG. 2) and 4 (FIG. 3) was much lower in the solvent mixture used for the hydrogenolysis (ethyl acetate/ethanol) than the tetraacid 1, and yields for this step ranged in both cases from approximately 35–55%, due primarily to problems with product recovery. Fortunately, subsequent trials proved that the diacids were also less soluble in water than the tetraacid, so saponification of either the ethyl or benzyl esters was a viable option; yields of the saponification reactions are routinely greater than 90%. Diacid Compound 3 precipitates immediately upon pouring the reaction mixture into 1M HCl, while diacid Compound 4 crystallizes when chilled overnight after pouring the reaction mixture into 1M HCl. Because the yields of all reaction steps in both syntheses are quite comparable using either ethyl or benzyl esters, it is preferred that benzyl esters be used for the simple reason that stockpiles of intermediates can be used in any synthesis, while ethyl ester derivatives could not be used in the synthesis of the glycoluril tetraacid. Otherwise, the ethyl hydantoate is available in one step from commercially available materials, while the benzyl hydantoate requires two steps, but the extra step is simple, high-yielding, and can be performed on a 100 g scale quite readily. A detailed description of the synthesis of core molecules can be found hereinafter in the Examples.

III Activation of Core Molecules for Library Construction

As is well known in the art, prior to use as core molecules for combinatorial library synthesis, it is necessary to activate the acid form of the molecule into a form suitable for library member or building block attachment. Historically, activation of core acids as acid chlorides has been a simple, effective way to accomplish this goal. In the case of the glycoluril core molecules, however, the presence of the urea functionality precludes activation as acid chlorides.

Fortunately, alternatives to acid chloride activation are numerous, as synthetic chemists have often found the need to synthesize amide bonds under milder reaction conditions than are required in the synthesis of acid chlorides. One option is to make use of a coupling reagent to directly couple the amine building blocks to the polyacid core. Another option is to activate the acids on the core as some functional group other than as acid chlorides and isolate the activated core for use in a subsequent amidation step. One unusual, but very important, criterion for the successful reaction in this case is that the final library-forming reaction must only produce by-products that can be totally removed by non-chromatographic methods. Since a wide variety of building blocks might be used in any given library synthesis, producing a number of compounds with potentially vastly different elution profiles, chromatographic techniques would be contraindicated if all library components are to be kept together as a mixture.

A preferred means of activating the core molecules of this invention is esterification. By way of example, diacid Compound 4 can be activated as the bis(pentafluorophenyl)ester (Compound 5, FIG. 4) by coupling the acids and pentafluorophenyl with EDC and catalytic DMAP in THF (see FIG. 4). The resulting active ester reacts readily with a variety of amines, including relatively unreactive anilines. Additionally, pentafluorophenyl can be removed by aqueous extraction during work-up. The glycoluril core is unaffected by the reaction conditions used for deprotection of t-butyl ester derivatives of amino acids used as building blocks (neat TFA, 12 h). A similar approach can be used to activate other forms of glycoluril polyacid core molecules (e.g., diacid Compound 3 or tetraacid Compound 1).

Figure 11:
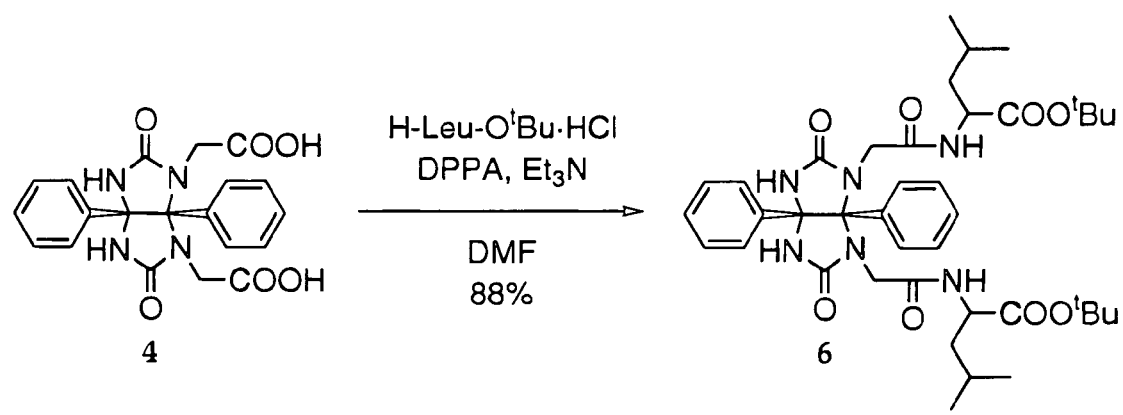
FIG. 11 shows an intermediate compound of this invention.

Another preferred means of activating the core molecules of this invention is by the use of amide coupling reagents to activate the acids in situ and react them directly with one or more building blocks (e.g., a substituted amine radical). A number of these coupling reagents are well known in the art. Some examples are dicyclohexyl carbodiimide (DCC), 1-(3-dimethylaminopropyl)-3-ethylcarbodiimide methiodide (EDCáMeI), benzotriazole-1-yl-oxy-tris-pyrrolidino-phosphonium hexafluorophosphate (PyBOP), bromo-tris-pyrrolidino-phosphonium hexafluorophosphate (PyBroP), and diphenylphosphoryl azide (DPPA). Many reactions using these coupling reagents work fairly well, but in some cases it is difficult to completely purify the products without resorting to chromatography. A preferred coupling reagent is DPPA. By way of example, diacid Compound 4 can be activated with DPPA and amine building blocks can be introduced directly on the core molecule (see FIG. 11). A similar approach can be used to activate other forms of glycoluril polyacid core molecules (e.g., diacid Compound 3 or tetraacid Compound 1).

IV Use in Forming Combinatorial Libraries

Solution phase synthesis has emerged as one method for the generating combinatorial libraries. By synthesizing the combinatorial library in solution, the present invention permits library synthesis that is more rapid and efficient than conventional methods, such as solid phase synthesis. Solid phase synthesis typically yields only a few nanograms of product. In contrast, the present invention, by synthesizing in solution, yields milligrams and grams of product.

A library is made by reacting a core molecule of this invention having activated carboxylic acid groups (e.g., $C_6F_5$), prepared as described above, with one or more building blocks (e.g., a substituted amine radical) under conditions and for a period of time sufficient for formation of the library member. Molecules in the soluble combinatorial library of the present invention may be purified by any of the techniques well known in the art. These techniques include, but are not limited to, precipitation, thin layer chromatography, column chromatography, high pressure liquid chromatography, crystallization, gel electrophoresis, and filtration.

A number a libraries have been synthesized using a core molecule of this invention. In particular, libraries using a core molecule according to Structure II and a number of substituted amines (Aniline, Benzylamine, Phenethylamine, 2,2-diphenyl ethylamine, Isobutylamine, Butylamine, N,N-diethylethylenediamine, 3 -(dimethylamino)propylamine, Aminomethyl cyclopropane, 4-amino-1-benzyl piperidine, 4-(3-aminopropyl)morpholine, 1-(3-aminopropyl)-2-pyrrolidinone, and Ethyl 4-amino-1-piperidine carboxylate) have been made.

The library can be screened to provide some measure of the activity of a library while not providing an opportunity to isolate the active compound(s) directly. A scheme wherein an initial large library is narrowed to a single active molecule depends initially on the synthesis of smaller sublibraries and in the final stages on active compound identification.

In a hypothetical example, assume that a library containing 3760 compounds (from the reaction of a mixture of 8 building blocks with glycoluril tetraacid core molecule having 1) is shown to be active in inhibiting the action of an enzyme in solution. In the next stage of deconvolution, 8 sublibraries, each of which lacks one of the original eight building blocks, is synthesized and assayed for activity. Those libraries that still demonstrate activity are known to contain the requisite building blocks for a potent inhibitor, while those sublibraries that are inactive are known to lack necessary building blocks. As each library has one fewer building block than the original active library, it is thus possible to look at the inactive sublibraries and read off the identity of each necessary building block. If there is more than one active compound in the original library, it is possible that more than four building blocks will be identified as important; additional sublibraries can then be synthesized to determine the most important of these, which would presumably correspond to those building blocks attached to the most potent inhibitor.

Once the most important four or fewer building blocks are identified, the relative geometries of the substituents on the core molecule in the active inhibitor can be determined by synthesizing the different isomers individually via the synthetic scheme disclosed and assaying them each individually (For related prior art relating to iterative screening processes, see Shipps et al., *Proc. Natl. Acad. Sci.,* 1997, 94, 11833–11838; Carell et al *Angew. Chem. Int. Ed.,* 1994, 33, 2061–2064).

In the more specific case where an activity screen is tied to a selection process, such as screening for tight binders by affinity chromatography, active compounds can be isolated from an initial large library. In this case, the identity of the molecule can be partially determined by mass spectrometry of the active compound itself or the building blocks isolated from the hydrolysis of the amide bonds in the active compound. However, at this point all that is known is the composition of the active, not its geometry. Again, synthesis of different isomers via the disclosed synthetic scheme is required to definitively assign the correct geometry to the active compound.

Figure 6:
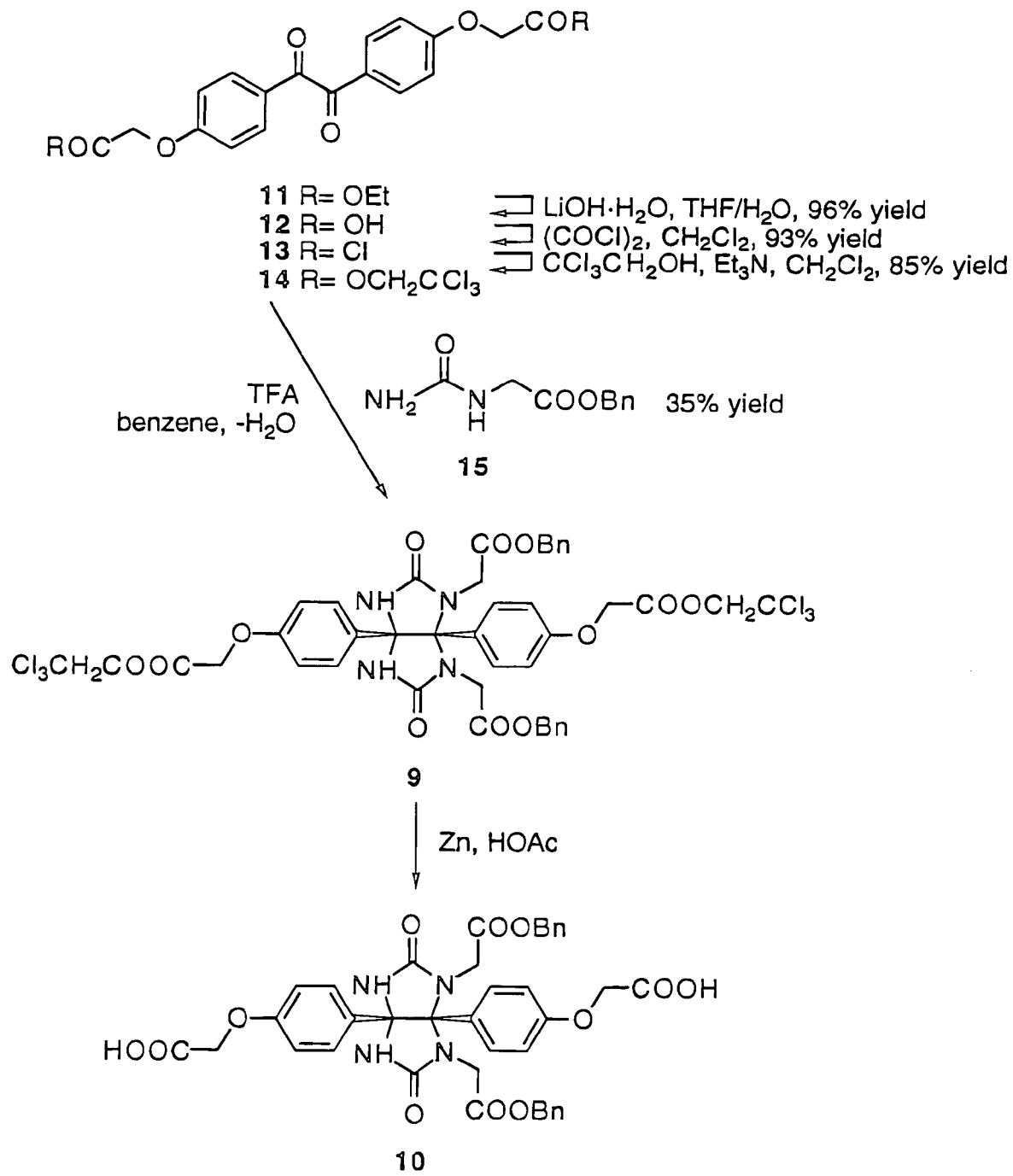
FIG. 6 shows the synthesis of certain heterotetrasubstituted glycoluril core molecules for use in stepwise library synthesis.
Figure 7:
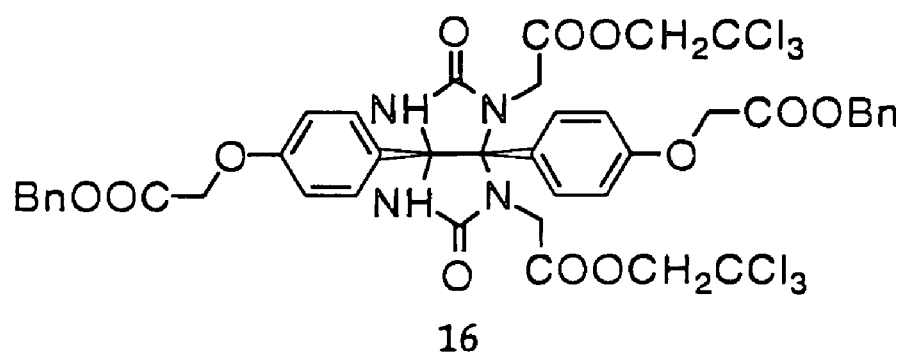
FIG. 7 shows an alternative heterotetrasubstituted glycoluril core molecules.

A synthetic scheme for diester/diacid 10 is shown in FIG. 6. This molecule incorporates different protecting groups into the molecule that allow orthagonal deprotection under conditions that would not epimerize aminoacid substituents. The diethyl ester substituted benzil 11 was saponified to 12 in almost quantitative yield with lithium hydroxide in aqueous THF. Conversion of this diacid to the diacid chloride 13 was accomplished using oxalyl chloride in good yield. Esterification with 2,2,2-trichloroethanol provided the protected dione 14.

The dione was condensed with benzyl hydantoate 15, available in two steps from glycine, to yield the differentially-protected glycoluril 9. Deprotection of the trichloroethyl esters was accomplished by treatment with zinc and acetic acid to give the diacid 10. Attempts to condense the free diacid 12 in a glycoluril-forming reaction only met with success when unsubstituted urea was used. In several attempts with benzyl hydantoate, the cyclization of the hydantoate to give hydantoin proceeded to the exclusion of the desired condensation; it is thought that the poor solubility of diacid 12 in the reaction medium is to blame.

Figure 8:
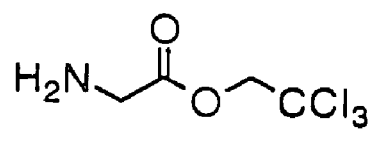
FIG. 8 shows novel intermediates used in the synthesis of selectively-deprotectable heteropolysubstituted glycoluril core molecules for deconvoluting molecular libraries.
Figure 8:
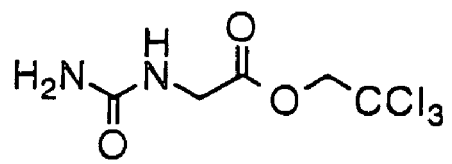

A synthesis of the "reverse" glycoluril 16 (FIG. 7), in which the benzyl and trichloroethyl esters are switched relative to compound 9, met with failure due to similar reasons. The trichloroethyl hydantoate is more labile to hydantoin formation than the benzyl analog, and glycoluril formation was not competetive in this case. All of the required precursors (trichloroethyl glycine 17 and trichloroethyl hydantoate 18, (FIG. 8) were synthesized, though, and are available for other use.

Figure 9:
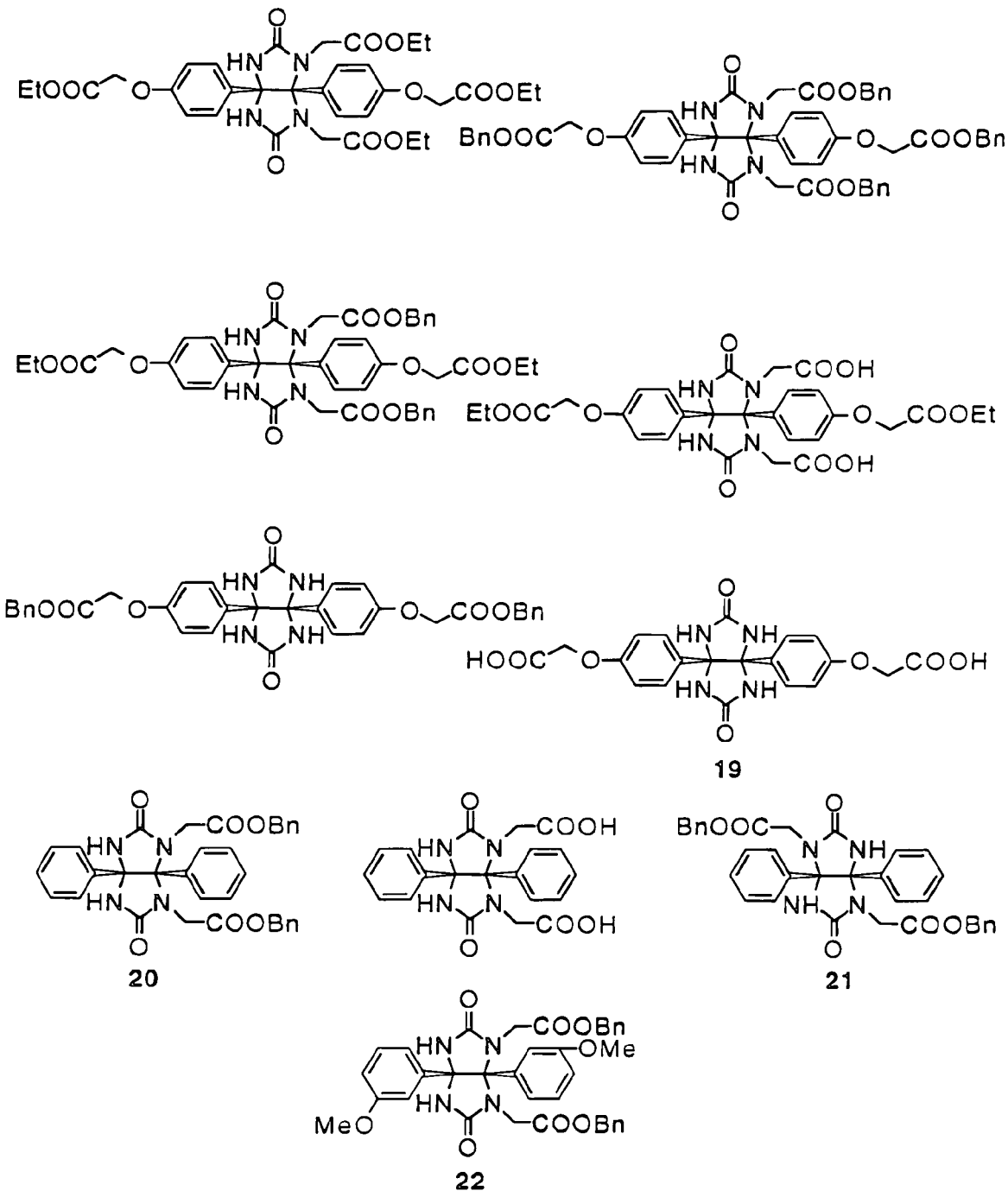
FIG. 9 shows several preferred core molecules of the current invention.

A selection of substituted glycoluril core molecules that have been prepared are shown in FIG. 9. Some of these compounds contain four carboxylates, while others have only two. Of those with two, 19 contains acids on the R groups coming from the starting dione, and 20, 21, and 22 contain esters coming from the starting urea (FIG. 9). It is interesting to note that the electron-donating substituents on the benzil precursors leading to all compounds except 20 and 21 prevent the formation of the trans-substituted compounds. In the case of 20 and 21, wherein the R groups are unsubstituted phenyls, a small amount of the trans isomer 21 was isolated, albeit in much lower yield (yields were 69% and 8%, respectively).

The Examples that follow illustrate preferred embodiments of the present invention and are not limiting of the specification and claims in any way.

EXAMPLE 1

General Methods

All reagents were purchased from Aldrich Chemical Company and were used without further purification except as noted. Amino acid esters, PyBOP, PyBrOP, and HATU were acquired from Novabiochem (San Diego, Calif.). Deuterated solvents were obtained from Cambridge Isotopes Laboratories and deuterated chloroform was dried over 4 Å molecular sieves. Citric acid and HCl refer to 1N stock solutions. NMR spectra were recorded on either a Bruker AC-250, a Bruker AM-300, or a Bruker DRX-600; TMS was used as a reference in chloroform-d proton spectra; otherwise residual solvent was used as a reference. Either a Finnegan Mat 8200 (for HRMS/EI) or a VG ZABVSE (for HRMS/FAB) mass spectrometer was used to ascertain exact masses. FT-IR spectra were obtained on a Perkin Elmer Paragon 1000 PC FT-IR Spectrometer. Silica gel chromatography was performed with Silica Gel 60 (EM Science or Bodman, 230400 mesh). TLC analysis was performed using glass-bound Silica Gel 60 (F254) plates. EDC.MeI=1-(3-dimethylaminopropyl)-3-ethylcarbodiimide methiodide. DMAP=N,N-dimethyl-4-aminopyridine.

EXAMPLE 2

Preparation of Glycoluril dibenzyl ester (Compound 3a, FIG. 2)

Dibenzyl 4,4'-bis(carboxymethoxy)benzil (43.82 g, 81.4 mmol) and urea (14.68 g, 244.4 mmol) (NOTE: 2.5 equivalents can also be used successfully) were dissolved in 400 mL benzene. TFA (20 mL) was added and the solution was refluxed under a Dean-Stark trap in a nitrogen atmosphere for 16 h. EtOH was added to the cooled solution and the solid precipitate was isolated by filtration. The solids were purified by stirring overnight in boiling EtOH. The resulting solids were isolated by filtration and dried in vacuo, yielding a white powder (36.97 g, 73%). $^1$H-NMR (600 MHz, DMSO-d$^6$): δ 7.65 (s, 4H), 7.33–7.38 (m, 10H), 6.94 (d, J=8.8 Hz, 4H), 6.65 (d, J=8.8 Hz, 4 H), 5.13 (s, 4H), 4.71 (s, 4H). $^{13}$C-NMR (151 MHz, DMSO-d$^6$): δ 168.66, 160.79, 157.24, 135.82, 131.30, 128.60, 128.42, 128.34, 128.20, 113.55, 81.60, 65.98, 64.56. Calc'd for [C$_{34}$H$_{30}$N$_4$O$_8$+Cs$^+$]: 755.1118; HRMS (FAB, NBA/CsI) found 755.1148. FT-IR (NaCl disc, cm$^{-1}$): 3229.6, 1760.0, 1721.7, 1682.8, 1667.3, 1610.2, 1494.5, 1454.6, 1416.5, 1175.5, 1140.7, 1110.5, 1082.9, 1024.5, 955.0, 836.7, 736.1, 696.6. m.p. 213–217° C. (dec.)

EXAMPLE 3

Preparation of Glycoluril diacid (Compound 3 from FIG. 2)

To a stirred suspension of glycoluril dibenzyl ester from Example 2 (1.00 g, 1.61 mmol) in 17.5 mL THF was added a solution of LiOH.H$_2$O (0.16 g, 3.9 mmol) in 3.5 μL water. The resulting mixture was vigorously stirred at RT for 17 h. The mixture was poured into 90 mL HCl. The resulting white solids were isolated by filtration and were dried at elevated temperature, yielding the diacid (0.68 g, 96%). $^1$H-NMR (600 MHz, DMSO-d$^6$): δ 7.66 (s, 4H), 6.94 (d, J=8.8 Hz, 4H), 6.62 (d, J=8, 7 Hz, 4H), 4.50 (s, 4H). $^{13}$C-NMR (151 MHz, DMSO-d$^6$): δ 160.90, 157.58, 130.98, 128.42, 113.55, 81.69, 64.72, 21.09. Calc'd for

[$C_{20}H_{18}N_4O_8$+H+]: 443.1203; HRMS (FAB, NBAlNaI) found 443.1233. FT-IR (DRAK, KBr, cm$^{-1}$): 3381, 3221 (br., v.s.), 2361, 1726, 1684, 1610, 1513, 1476, 1445, 1419, 1302, 1235, 1185, 1110, 1074, 954, 839, 780, 737, 634. m.p. 287° C. (dec.)

EXAMPLE 4

Preparation of Glycoluril diacid (Compound 4 from FIG. 3):

A solution of LiOH.H$_2$O (0.101 g, 2.40 mmol) in 21 mL water was added to a stirred suspension of glycoluril dibenzyl ester from Example 2 (0.590 g, 1.00 mmol) in 10 mL THF. This mixture was stirred at RT for 16 h, then was poured into 50 mL HCl. The resulting solution was chilled in a refrigerator. Clear crystals grew in the solution, which were isolated by filtration and were dried at elevated temperature, yielding the diacid (0.37 g, 90%). $^1$H-NMR (600 MHz, DMSO-d$^6$): δ 12.62 (br. S, 2H {integrated low}), 8.21 (s, 2H), 7.07 (s, 10H), 3.90 (d, J=17.6 Hz, 2H), 3.62 (d, J=17.6 Hz, 2H). $^{13}$C-NMR (151 MHz, DMSO-d$^6$): δ 171.06, 159.54, 137.87, 133.96, 128.79, 128.38, 128.35, 128.19, 127.62, 127.51, 88.64, 79.90, 43.08. Calc'd for [$C_{20}H_{18}N_4O_6$+H+]: 411.1305; HRMS (FAB, NBA/NaI) found 411.1317. FT-IR (DRAK, KBr, cm$^{-1}$): 3456.6, 3228.0 (br.), 1734.8, 1700.2, 1474.6, 1449.8, 1399.8, 1340.7, 1225.6, 1147.2, 985.8, 963.9, 944.5, 780.7, 703.7, 667.9. m.p. 255° C. (dec.)

EXAMPLE 5

Figure 4:
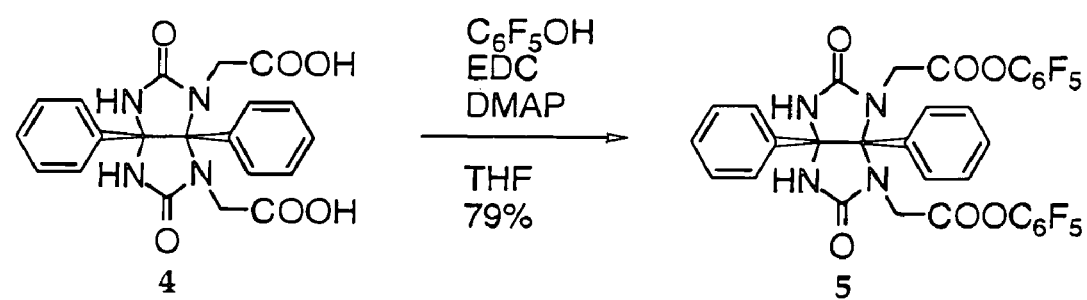
FIG. 4 shows one way to activate certain disubstituted core molecules.
Figure 5:
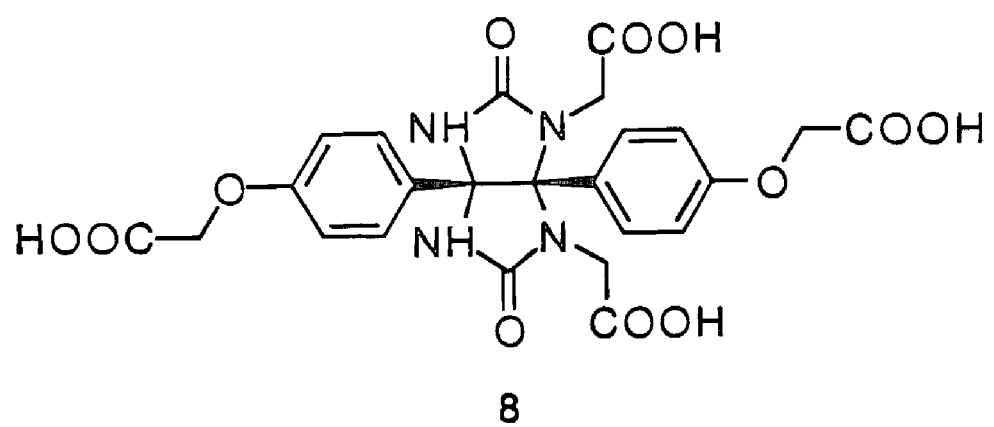
FIG. 5 shows one embodiment of a core molecule with the invention.

Preparation of Glycoluril bis(pentafluorophenyl ester (Compound 5 from FIG. 4)

To a stirred suspension of glycoluril diacid 4 from Example 4 (1.00 g, 2.44 mmol) in 100 mL THF was added pentafluorophenyl (1.80 g, 9.76 mmol), EDC.MeI (3.12 g, 10.5 mmol) and catalytic DMAP. The mixture was stirred at RT for 14 h. The solvent was removed by rotary evaporation and the resulting paste was sonicated in EtOAc and filtered to remove insoluble material. The filtrate was run through a plug of silica gel with EtOAc. The filtrate was concentrated and sonicated in Et$_2$O to remove pentafluorophenyl. The white powder was isolated by filtration, rinsed with Et$_2$O and dried in vacuo, yielding the diester (1.42 g, 79%). $^1$H-NMR (600 MHz, DMSO-d$^6$): δ 8.58 (s, 2H), 7.15–7.03 (m, 10H), 4.77 (d, J=18.4 Hz, 2H), 4.38 (d, J=18.4 Hz, 2H). $^{13}$C-NMR (151 MHz, DMSO-d$^6$): δ 166.77, 159.03, 141.52 (m), 139.83 (m), 138.54 (m), 137.06, 136.89 (m), 133.31, 129.08, 128.55, 127.79, 127.69, 127.31, 88.34, 80.48, 42.39. $^{19}$F-NMR (565 MHz, DMSO-d$^6$): δ-152.61 (d, J=24 Hz), −157.44 (t, J=24 Hz), −162.16 (t, J=24 Hz). Calc'd for [$C_{32}H_{16}F_{10}N_4O_6$+Cs+]: 874.9964; HRMS (FAB, NBA/CsI) found 875.0004. FT-IR (NaCl disc, cm$^{-1}$): 1788.7, 1714.4, 1521.7, 1450.0, 1103.7, 998.1.

EXAMPLE 6

Figure 10:
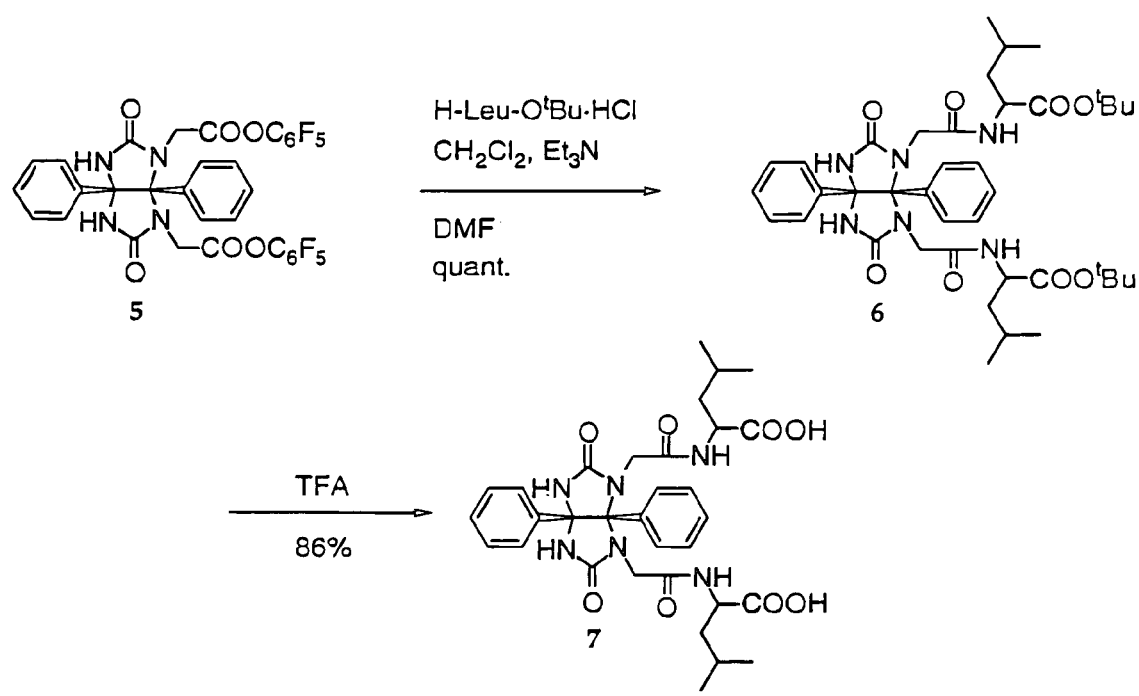
FIG. 10 shows a preferred embodiment for library formation using one activated disubstituted glycoluril core molecule.

Preparation of Glycoluril bis(leucine t-butyl ester) adduct (Compound 6 from FIG. 10)

A. Reaction of bis(pentafluorophenyl ester). To a solution of leucine t-butyl ester hydrochloride (34.8 mg, 0.155 mmol) in 1 mL DMF and 0.5 mL Et$_3$N chilled in an ice bath was added a partial solution/suspension of glycoluril bis(pentafluorophenyl ester) Compound 5 (50.4 mg, 0.0683 mmol) in 3.5 mL CH$_2$Cl$_2$. The solution warmed over 2.5 h, then was diluted with CH$_2$Cl$_2$ and was washed with water (3×) and brine (3×). The organic phase was dried over MgSO$_4$, was filtered, and was concentrated by rotary evaporation to pale yellow solids which were dried in vacuo (53 mg, quant.)

B. Reaction of diacid with DPPA. A stirred solution of glycoluril diacid Compound 4 (200 mg, 0.487 mmol) and of leucine t-butyl ester hydrochloride (240 mg, 1.07 mmol) in 2 mL DMF was chilled in a salt/ice bath. To this solution was added diphenylphosphoryl azide (231 μL, 294 mg, 1.07 mmol) and Et$_3$N, (298 μL, 217 mg, 2.14 mmol) and the solution was stirred 17 h, warming to RT. The solvent was removed by rotary evaporation and the residue was taken up in EtOAc and was washed with water (2×) and brine (3×). The organic phase was dried over MgSO$_4$, was filtered, and was concentrated by rotary evaporation to an off-white foam (323 mg, 88%). $^1$HNMR (600 MHz, CDCl$_3$): δ 7.24–7.21 (m, 2H), 7.16–6.97 (m, 10H), 6.85 (br. s, 1H), 6.78 (br. s, 1H), 4.41–4.37 (m, 2H), 3.95 (d, J=16.3 Hz, 1H), 3.82 (s, 2H), 3.65 (d, J=16.5 Hz, 1H), 1.70–1.46 (m, 6H), 1.44 (s, 9H), 1.42 (s, 9H), 0.95 (d, J=6.6 Hz, 3 H), 0.93 (d, J=6.5 Hz, 3H), 0.93 (d, J=6.4 Hz, 3H), 0.88 (d, J=6.4 Hz, 3H).). $^{13}$CNMR (151 MHz, CDCl$_3$): δ 172.57, 172.41, 168.57, 168.52, 160.98, 160.59, 136.57, 131.90, 129.51, 129.38, 129.00, 128.82, 1283.63, 128.27, 127.57, 123.48, 120.50, 120.47, 90.79, 82.10, 82.02, 80.69, 51.93, 51.75, 45.96, 45.79, 41.46, 41.33, 28.08, 28.06, 25.00, 24.98, 22.83, 22.74, 22.33, 22.21. Calc'd for [$C_{40}H_{56}N_6O_8$+Na+]: 771; LRMS (FAB, NBA/NaI) found 771. FT-IR (NaCl disc, cm$^{-1}$): 3242.3, 2958.7, 1701.9, 1458.4, 1150.0.

EXAMPLE 7

Preparation of Glycoluril bis(leucine) adduct (Compound 7, FIG. 10)

Glycoluril bis(leucine t-butyl ester adduct) Compound 6 (45 mg, 0.060 mmol) was stirred in 5 mL TFA for 15 h. The TFA was removed by rotary evaporation and the resulting oil was sonicated in 1:1 Et$_2$O:hexane. The resulting precipitate was isolated by filtration and was rinsed with Et$_2$O, yielding a white powder (34 mg, 86%). $^1$H-NMR (600 MHz, DMSO-d$^6$): δ 8.27 (s, 1H), 8.25 (s, 1H), 7.96 (d, J=7.9 Hz, 1H), 7.79 (d, J=7.8 Hz, 1H), 7.09–7.02 (m, 10H), 4.28–4.26 (m, 2H), 3.85 (d, J=16.6 Hz, 1H), 3.66 (d, J=16.8 Hz, 1H), 3.53 (d, J=16.7 Hz, 1H), 3.52 (d, J=16.8 Hz, 1H), 1.79–1.70 (m, 1H), 1.70–1.62 (m, 1H), 1.55–1.48 (m, 4H), 0.92–0.85 (m, 12H). $^{13}$C-NMR (151 MHz, DMSO-d$^6$): δ 174.42, 174.19, 168.47, 168.39, 159.73, 159.69, 137.62, 133.37, 128.72, 128.26, 127.49, 127.36, 89.12, 79.61, 50.30, 45.77, 44.22, 44.05, 40.28, 24.21, 22.85, 22.79, 21.41, 8.58. Calc'd for [$C_{32}H_{40}N_6O_8$+Cs+]: 769; LRMS (FAB, NBA/CsI) found 769.

EXAMPLE 8

Preparation of Glycoluril tetrakis(pentafluorophenyl ester)

A solution of glycoluril tetraacid (200 mg, 0.358 mmol), pentafluoro-phenyl (527 mg, 2.86 mmol), EDC-MeI (847 mg, 2.85 mmol), and catalytic DMAP in 20 mL THF was stirred at RT for 8 h. The solvent was removed by rotary evaporation and the residue was taken up in EtOAc and shaken. Insoluble material was removed by filtration and the filtrate was concentrated and purified by silica gel chromatography (100% EtOAc). Product-containing fractions were combined and concentrated by rotary evaporation. Excess pentafluorophenyl co-eluted with the product and was removed by sonicating the resulting oil in Et$_2$O. White solids were isolated by filtration and were dried in vacuo (62 mg, 15%). $^1$H-NMR (600 MHz, DMSO-d$^6$): δ 8.53 (s, 2H), 6.99 (d, J=8.8 Hz, 2H), 6.98 (d, J=8.7 Hz, 2H), 6.76 (d, J=8.3 Hz, 4H), 5.22 (s, 2H), 5.21 (s, 2H), 4.77 (d, J=18.3 Hz, 2H), 4.37 (d, J=18.3 Hz, 2H). Calc'd for [C$_{48}$H$_{18}$F$_{20}$N$_4$O$_{12}$+H+]: 1223.0680; HRMS (FAB, NBA/CsI) found 1223.0609.

What is claimed is:

1. A compound of the structure I, below

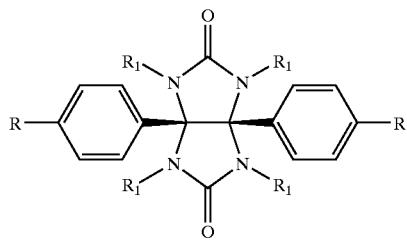

I where each R is independently hydrogen or —OR$_1$, each R$_1$ is independently hydrogen or CH$_2$COOR$_2$ and each R$_2$ is independently hydrogen, C$_1$–C$_6$ alkyl, C$_1$–C$_6$ alkenyl, C$_1$–C$_6$ alkynyl, C$_6$ aryl, or C$_6$–C$_9$ aralkyl, with the proviso that at least R$_1$ be CH$_2$COOR$_2$.

2. The compound of claim 1 wherein each R is hydrogen.
3. The compound of claim 1 wherein each R is OR$_1$.
4. The compound of claim 1 wherein two of the R$_1$ groups are hydrogen.
5. The compound of claim 1 wherein each R is OR, and two of the R$_1$ groups are hydrogen.
6. The compound of claim 1 wherein R$_2$ is a C$_6$ aryl.
7. The compound of claim 6 wherein the C$_6$ aryl is a halo-substituted C$_6$ aryl.
8. The compound of claim 7 wherein the halo-substituted C$_6$ aryl is C$_6$F$_5$.
9. The compound of claim 1 wherein R$_2$ is a C$_2$ alkyl.
10. The compound of claim 9 wherein the C$_2$ alkyl is ethyl.
11. The compound of claim 9 wherein the C$_2$ alkyl is halo-substituted C$_2$ alkyl.
12. The compound of claim 11 wherein the halo-substituted C$_2$ alkyl is 2,2,2-trichloroethyl.
13. The compound of claim 1 wherein R$_2$ is a C$_7$ aralkyl.
14. The compound of claim 13 wherein the C$_7$ aralkyl is benzyl.
15. The compound of claim 1 having the structure

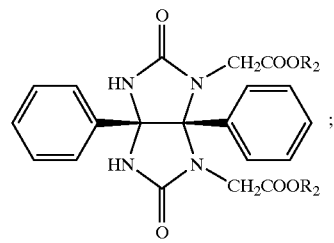

;

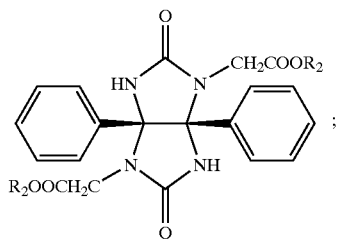

;

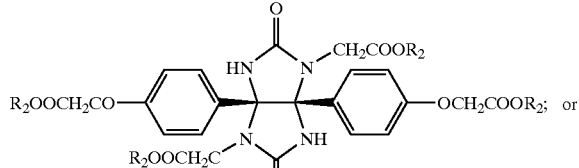

; or

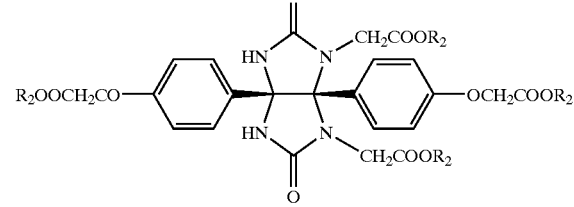

* * * * *